US00PP30911P3

(12) United States Plant Patent
Austin

(10) Patent No.: US PP30,911 P3
(45) Date of Patent: Oct. 1, 2019

(54) ***ROSA HYBRIDA* SHRUB NAMED 'AUSQUAKER'**

(50) Latin Name: *Rosa hybrida*
Varietal Denomination: AUSquaker

(71) Applicant: David Austin Roses Ltd., Albrighton, Wolverhampton (GB)

(72) Inventor: David J. C. Austin, Albrighton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 15/932,842

(22) Filed: May 3, 2018

(65) Prior Publication Data

US 2019/0098811 P1 Mar. 28, 2019

(30) Foreign Application Priority Data

Sep. 26, 2017 (GB) ..... PBR 5/2136
Oct. 3, 2017 (EP) ..... 2017/2476

(51) Int. Cl.
*A01H 5/02* (2018.01)
*A01H 6/74* (2018.01)

(52) U.S. Cl.
USPC ..... Plt./106
CPC ..... *A01H 6/749* (2018.05)

(58) Field of Classification Search
USPC ..... Plt./106
See application file for complete search history.

*Primary Examiner* — Anne Marie Grunberg
(74) *Attorney, Agent, or Firm* — KPPB LLP

(57) ABSTRACT

A variety of rose plant of the shrub class, named 'AUSquaker'. The 'AUSquaker' is a variety of a rose shrub with blooms containing two-colored petals, yellow from the base to the middle, blending towards an orange top half of the petal. The overall appearance is of rich apricot blooms, which begin as striking, red-tipped buds and gradually open to reveal large informal rosettes, each with ruffled petals and a button eye. They are very resistant to rain damage and the petals drop neatly. The fragrance is light-medium tea. The plant is a vigorous grower producing strong, arching stems and particularly reliable and healthy.

1 Drawing Sheet

Figure 3:
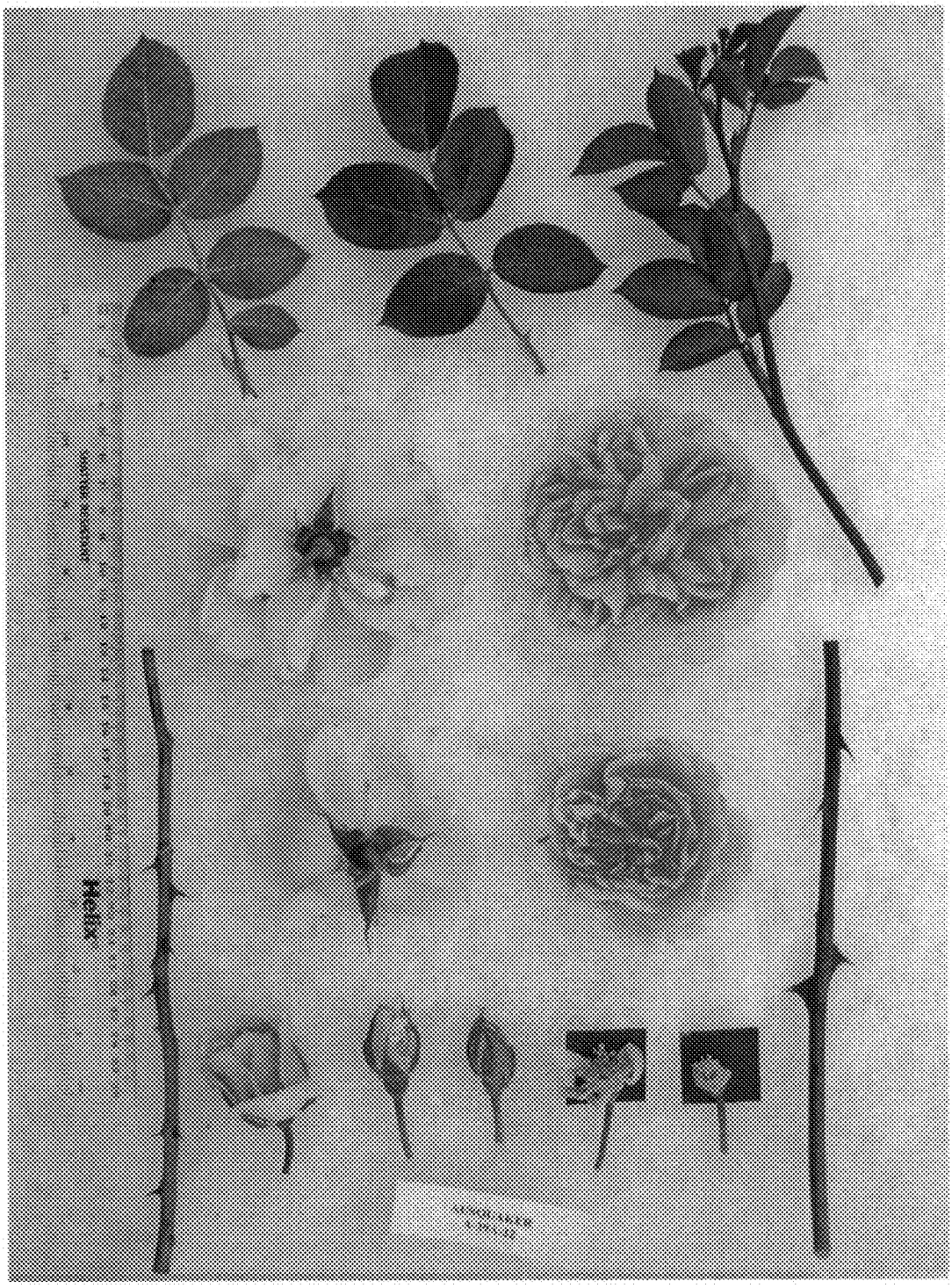

Classification: The present invention relates to a new *Rosa hybrida* shrub of the market class 'English Rose'.

Variety denomination: The new plant has the varietal denomination 'AUSquaker'.

CROSS-REFERENCE TO RELATED APPLICATION

The present application claims priority to UK Plant Patent No. 5/2136, filed Sep. 26, 2017, and European CPVO 2017/2476, filed Oct. 3, 2017.

ORIGIN OF INVENTION

This invention relates to a new and distinct variety of shrub rose plant named 'AUSquaker', which was originated from the cross-pollination of the two 'unnamed' and unpatented seedlings of *Rosa hybrida.*

BACKGROUND OF THE INVENTION

The primary objective of this breeding was to produce a rose variety with blooms containing two-colored petals, yellow from the base to the middle, blending towards an orange top half of the petal. The overall appearance is of rich apricot blooms, which begin as striking, red-tipped buds and gradually open to reveal large informal rosettes, each with ruffled petals and a button eye. They are very resistant to rain damage and the petals drop neatly. The fragrance is light-medium tea. The plant is a vigorous grower producing strong, arching stems and particularly reliable and healthy.

SUMMARY OF THE INVENTION

Among the features which distinguish the new variety from others presently available and commercial rose cultivars known to the inventor is the following combination of characteristics: two-colored petals resulting in a rich apricot bloom, red-tipped buds, large informal rosette-shaped blooms, ruffled petals, button eyes, blooms that are resistant to rain damage, and vigorous arching stems.

Asexual reproduction of the new variety by budding as performed at Bowling Green Lane in Albrighton, Britain shows that the foregoing and other distinguishing characteristics come true to form and are established and transmitted through succeeding asexual propagations. 'AUSquaker' may be asexually propagated by budding. The budding successfully occurred on the plant/rootstock *Rosa* 'Dr. Huey' in the US and *Rosa dumetorum* in the UK for the observed plants.

COMPARISON WITH PARENTS

The maternal and paternal parents of 'AUSquaker' are two unnamed seedlings. The new rose may be distinguished from its maternal parent, by the following combination of characteristics: the maternal parent is cream with a deep cupped bloom and upright growth, as opposed to the shallower rosettes and arching growth of 'AUSquaker'. The new rose may be distinguished from its pollen parent, by the following combination of characteristics: the paternal parent was apricot pink with upright growth, whereas 'AUSquaker' is a rich apricot with yellow coloring and arching growth.

COMPARISON WITH THE CLOSEST COMMERCIALLY AVAILABLE CULTIVAR

The closest commercially available cultivars to the new variety are the 'AUSbrass' (unpatented) and 'AUSlofty' (U.S. Plant Pat. No. 19,875). The new rose may be distinguished from the 'AUSbrass' based on the fact that 'AUSbrass' has quartered formation and light green colored new wood, whereas 'AUSquaker' has brown/red new wood and unquartered blooms. 'AUSbrass' is also pricklier than 'AUSquaker'. 'AUSlofty' has blooms that are smaller in diameter and deeper than 'AUSquaker', and the growth of 'AUSlofty' is upright while 'AUSquaker' is arching.

BRIEF DESCRIPTION OF ILLUSTRATION

The accompanying photograph illustrates the new variety and shows the flowering thereof from bud to full bloom depicted in color as nearly correct as it is possible to make in a color illustration of the character.

Throughout this specification, color references and/or values are based upon The Colour Chart of The Royal Horticultural Society (2001) except where common terms of color definition are employed.

DESCRIPTION OF THE NEW VARIETY

Observations of budded 'AUSquaker' specimens were made at the nursery at David Austin Roses Limited in Albrighton, Wolverhampton, United Kingdom. The following description is of 1 year-old rose plants of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.5 cm long and 1.6 cm in diameter when the petals start to unfurl.

*Form*.—The bud form is blunt topped.

*Color*.—When sepals first divide, the bud color is RHS 20A (yellow-orange group) with RHS 60A (red-purple group). When half blown, the upper sides of the petals are RHS 24A (orange group), and the lower sides of the petals RHS 29A (orange group).

*Calyx*.—Shape: star shape, folding back against the stem when the flower is fully open. Length: 6.5 cm. Diameter: 6.5 cm.

*Sepals*.—Arrangement: Regularly arranged. Color: Upper Surface: RHS 138C (green group). Lower Surface: RHS 144A (yellow-green group) with RHS 184A (greyed-purple group). Length: 2.6 cm. Width: 7 mm. Shape: Lanceolate. Surface texture: Upper Surface: Downy. Lower Surface: Smooth. Number: There are 3 lightly appendaged sepals, and 2 unappendaged sepals with glandular edges. The Sepal extensions are weak.

*Receptacles*.—Color: RHS 144A (yellow-green group). Shape: Funnel. Size: Medium, about 1 cm long×9 mm wide. Surface: Smooth.

*Peduncle*.—Length: Medium, averaging about 6.5 cm. Surface: Smooth. Color: RHS 144A (yellow-green group). Strength: Weak.

Blooms:

*Size*.—Large, average open diameter is about 10.5 cm.

*Borne*.—Several together usually with 3 to 6 blooms together with inflorescence having a rounded shape.

*Stems*.—Strength: Normal, average length is about 35 cm. Diameter: 5 mm.

*Form*.—When first open, bloom is cupped. Permanence of bloom: outer petals curl back.

*Type*.—Double.

Petalage: Number of petals under normal conditions: 76.

*Color*.—The upper sides of the petals are RHS 23B (yellow-orange group) at the middle and RHS 29B (orange group) at the top. The reverse sides of the petals are RHS 23B (yellow-orange group) at the middle and RHS 29B (orange group) at the top. The base of the petals has a spot that is RHS 12A (yellow group).

*Variegations*.—None.

*Discoloration*.—The general tonality at the end of the first day is RHS 24A (orange group), and at the end of the third day is RHS 24A (orange group). With further aging turns RHS 16B (yellow-orange group) particularly on outer petals.

*Fragrance*.—Slight. Character of fragrance: Tea.

Petals:

*Texture*.—Smooth.

*Size*.—Width: 3.4 cm. Length: 4.3 cm.

*Surface*.—Smooth.

*Shape*.—Obovate.

*Margin*.—Entire.

*Apex shape*.—Rounded.

*Base shape*.—Acute.

*Form*.—Incurved.

*Arrangement*.—Informal.

*Petaloids*.—Number: Few, around 3-7. Color: RHS 29A (orange group). Length: between 1-2.5 cm. Width: between 0.5-1.5 cm. Shape: Deformed petal, some crescent-shaped, the shape of a half-petal. Margin: Irregular.

*Persistence*.—Petals drop off cleanly before drying.

*Lastingness*.—On the plant: Fair. As a cut flower: not tested.

Reproductive parts:

*Stamens*.—Number: 80 approximately. Length: 7 mm.

*Anthers*.—Length: 2 mm. Color: RHS 15A (yellow-orange group). Arrangement: Regular around styles with some partly tucked in calyx.

*Filaments*.—Color: RHS 16A (yellow group). Length: 5 mm.

*Pollen*.—Color: RHS 17A (yellow-orange group). Amount: Moderate.

*Pistils*.—Number: 30. Length: 5 mm.

*Styles*.—Color: RHS 67B (red-purple group). Length: 4 mm.

*Stigmas*.—Color: RHS 163B (greyed-orange group). Length: 1 mm.

*Hips*.—NONE Observed.

PLANT CHARACTERISTICS

Plant form: Shrub.

Plant growth: Vigorous and arching.

Age to maturity: 2 years.

Mature plant: Height: 1.2 m. Width: 1.2 m.

Rootstock: 'Dr Huey' in the US and *Rosa dumetorum* 'Laxa' for the observed plants in the UK. Neither rootstock is patented in the US.

Foliage:

*Number*.—Leaflets on normal mid-stem leaves is: 5 (including terminal leaflet).

*Size*.—Medium, about 14 cm long×9 cm wide.

*Quantity*.—Normal. Number of leaves per flowering stem is: 7-10.

*Color*.—New foliage: Upper side: RHS 147A (yellow-green group) tinged with RHS 183B (greyed-purple group). Lower side: RHS 147B (yellow-green group). Old foliage: Upper side: RHS 139A (green group). Lower side: RHS 137C (green group).

Leaflets:

*Size*.—About 5 cm long×3.8 cm wide.

*Shape*.—Pointed oval.

*Base shape*.—Rounded.

*Apex shape*.—Acuminate.

*Texture*.—Smooth.

*Glossiness*.—Strong.

*Edge*.—Serrated.

*Serrations*.—Single.

*Petiole*.—Color: RHS 144A (yellow-green group). Length: 4 cm. Width: 1.5 mm. Surface Texture: glandular.

*Petiole rachis*.—Color: RHS 144A (yellow-green group). Underside: with prickles.

*Stipules*.—Length: 2.1 cm, glandular. Color: RHS N144A (yellow-green group).

*Auricle*.—Shape: Lanceolate. Length: 6 mm. Width: 2 mm. Color: RHS N144A (yellow-green group).

*Vein color*.—Color: Upper side: RHS 139A (green group). Lower side: RHS 137C (green group).

*Venation pattern*.—Reticulate.

Wood:

*New wood*.—Color: RHS 183A (greyed-purple group). Bark: Smooth.

*Old wood*.—Color: RHS 144A (yellow-green group). Bark: Smooth.

Branching habit:

*Number*.—20.

*Lateral branch dimensions*.—Length: 30 cm. Diameter: 5 mm.

Stems:

*Mature stem*.—Length: 60 cm. Diameter: 7 mm.

*Internode distance*.—5 cm. The above measurements are all variable, depending on growing conditions in a season.

*Stem pubescence present*.—No.

Prickles:

*Quantity*.—On main canes from base: Ordinary. Number per stem length: 12 per 20 cm. On laterals from main canes: Ordinary. Number per stem length: 12 per 20 cm.

*Form*.—Deep concave.

*Length*.—8 mm.

*Color when young*.—RHS 183A (greyed-purple group) with RHS 144A (yellow-green group) tips.

*Color when mature*.—RHS 183A (greyed-purple group).

Small prickles:

*Quantity*.—Main stalk: None. Laterals: None.

Disease resistance:

*Powdery mildew* (*Podosphaera pannosa*).—Resistant.

*Downy mildew* (*Peronospora species*).—Resistant.

*Blackspot* (*Diplocarpon rosae*).—Resistant.

*Rust* (*Phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class, substantially as herein shown and described.

* * * * *